(12) United States Patent
Maltz

(10) Patent No.: US 11,383,104 B2
(45) Date of Patent: Jul. 12, 2022

(54) SYSTEMS AND METHODS FOR DOSE MEASUREMENT IN RADIATION THERAPY

(71) Applicant: UIH AMERICA, INC., Huston, TX (US)

(72) Inventor: Jonathan Maltz, Huston, TX (US)

(73) Assignee: UIH AMERICA, INC., Houston, TX (US)

( * ) Notice: Subject to any disclaimer, the term of this patent is extended or adjusted under 35 U.S.C. 154(b) by 189 days.

(21) Appl. No.: 16/914,361

(22) Filed: Jun. 27, 2020

(65) Prior Publication Data

US 2020/0324144 A1 Oct. 15, 2020

(51) Int. Cl.
*A61N 5/10* (2006.01)
*G06T 7/00* (2017.01)

(52) U.S. Cl.
CPC ......... *A61N 5/1039* (2013.01); *A61N 5/1045* (2013.01); *G06T 7/0012* (2013.01); *A61N 2005/1034* (2013.01); *A61N 2005/1054* (2013.01)

(58) Field of Classification Search
CPC ...... A61N 5/10; A61N 5/1039; A61N 5/1045; A61N 5/103; A61N 5/1071; A61N 5/1075; A61N 5/1065; A61N 5/1049; A61N 2005/1034; A61N 2005/1054; G06T 7/00; G06T 7/0012
See application file for complete search history.

(56) References Cited

U.S. PATENT DOCUMENTS

| 8,130,905 B1 | 3/2012 | Nelms | |
| 2020/0199705 A1 | 6/2020 | Terashima et al. | |
| 2020/0206539 A1* | 7/2020 | Han | A61N 5/1075 |
| 2021/0113857 A1* | 4/2021 | Maltz | A61N 5/1071 |
| 2021/0187326 A1* | 6/2021 | Han | A61N 5/103 |

* cited by examiner

*Primary Examiner* — Jurie Yun
(74) *Attorney, Agent, or Firm* — Metis IP LLC

(57) ABSTRACT

The present disclosure provides a system and method for medical imaging. The method may include obtaining a treatment plan, a planning image, and one or more treatment images of the subject, wherein the one or more treatment images are generated by performing at least a portion of the treatment plan including delivering at least a radiation beam towards the subject using a radiation device. The method also includes determining primary images of the subject based on the one or more treatment images, and determining inversely-attenuated primary images of the subject by inversely attenuating the primary images to a plane located between the subject and a collimator assembly of the radiation device. The method may further include estimating machine parameters of the radiation device corresponding to the inversely-attenuated primary images.

20 Claims, 9 Drawing Sheets

SYSTEMS AND METHODS FOR DOSE MEASUREMENT IN RADIATION THERAPY

TECHNICAL FIELD

The present disclosure generally relates to radiation therapy, and more particularly, to systems and methods for radiation dosimetry in a radiation therapy.

BACKGROUND

Radiation therapy is widely used in cancer treatment and several other health conditions. Usually, a radiation therapy treatment plan (also referred to as a treatment plan) for a patient is generated before treatment starts. Radiation doses may be delivered, according to the treatment plan, to the patient in several treatment fractions. In this process, an actual dose delivered to the patient may be different from the planned dose due to factors including, e.g., a penumbra region around edges of a treatment field defined by a collimator assembly. Thus, it may be desirable to develop systems and methods for measuring an actual dose delivered during radiation treatment.

SUMMARY

According to an aspect of the present disclosure, a system is provided. The system may include at least one storage device including a set of instructions, and at least one processor configured to communicate with the at least one storage device. When executing the set of instructions, the at least one processor may be configured to direct the system to perform the following operations. The following operations may include obtaining a treatment plan and a planning image of a subject; obtaining one or more treatment images of the subject, wherein the one or more treatment images are generated by performing at least a portion of the treatment plan including delivering at least a radiation beam towards the subject using a radiation device; determining primary images of the subject based on the one or more treatment images; determining inversely-attenuated primary images of the subject by inversely attenuating the primary images to a plane located between the subject and a collimator assembly of the radiation device; and estimating machine parameters of the radiation device corresponding to the inversely-attenuated primary images.

In some embodiments, the one or more treatment images includes electronic portal imaging device (EPID) images.

In some embodiments, the determining inversely-attenuated primary images of the subject by inversely attenuating the primary images to a plane between the subject and a collimator assembly of the radiation device includes obtaining a penumbra model associated with penumbra characteristics of edges of the collimator assembly; and determining the inversely-attenuated primary images of the subject by inversely attenuating the primary images to the plane based at least in part on the penumbra model.

In some embodiments, the penumbra characteristics of the edges of the collimator assembly are determined based on a look-up table, wherein the look-up table relates to at least one of a medium-equivalent thickness of the subject, one or more elements of the collimator assembly, a position of each of at least one element of the collimator assembly, or beam quality of the radiation device.

In some embodiments, the look-up table further relates to a plurality of tissue types and a dimension of each of at least one of the plurality of tissue types of the subject.

In some embodiments, the penumbra characteristics of edges of the collimator assembly are determined based on a forward transport of a treatment field through the subject.

In some embodiments, the forward transport includes a Monte Carlo simulation or a Boltzmann transport algorithm.

In some embodiments, the forward transport has a perturbation range associated with penumbra regions in the one or more treatment images.

In some embodiments, scatter in the forward transport is determined according to a kernel based algorithm.

In some embodiments, the operations further including determining an input fluence map based on the inversely-attenuated primary images of the subject; and determining an estimate of a dose delivered to the subject by inputting the input fluence map into a forward dose calculation algorithm.

In some embodiments, the machine parameters correspond to a planned dose to be delivered to the subject.

According to another aspect of the present disclosure, a system is provided. The system may include at least one storage device including a set of instructions, and at least one processor configured to communicate with the at least one storage device. When executing the set of instructions, the at least one processor may be configured to direct the system to perform the following operations. The following operations may include obtaining a treatment plan and a planning image of a subject; obtaining one or more treatment images of the subject, wherein the one or more treatment images are generated by performing at least a portion of the treatment plan including delivering at least a radiation beam towards the subject using a radiation device; determining primary images of the subject based on the one or more treatment images; determining inversely-attenuated primary images of the subject by inversely attenuating the primary images to a plane located between the subject and a collimator assembly of the radiation device based at least in part on a penumbra model associated with penumbra characteristics of edges of the collimator assembly; and determining an input fluence map based on the inversely-attenuated primary images of the subject; and estimating a dose delivered to the subject by inputting the input fluence map into a forward dose calculation algorithm.

According to a further aspect of the present disclosure, a method implemented on a computing device having a processor and a computer-readable storage device is provided. The method may include obtaining a treatment plan and a planning image of a subject; obtaining one or more treatment images of the subject, wherein the one or more treatment images are generated by performing at least a portion of the treatment plan including delivering at least a radiation beam towards the subject using a radiation device; determining primary images of the subject based on the one or more treatment images; determining inversely-attenuated primary images of the subject by inversely attenuating the primary images to a plane located between the subject and a collimator assembly of the radiation device; and estimating machine parameters of the radiation device corresponding to the inversely-attenuated primary images.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
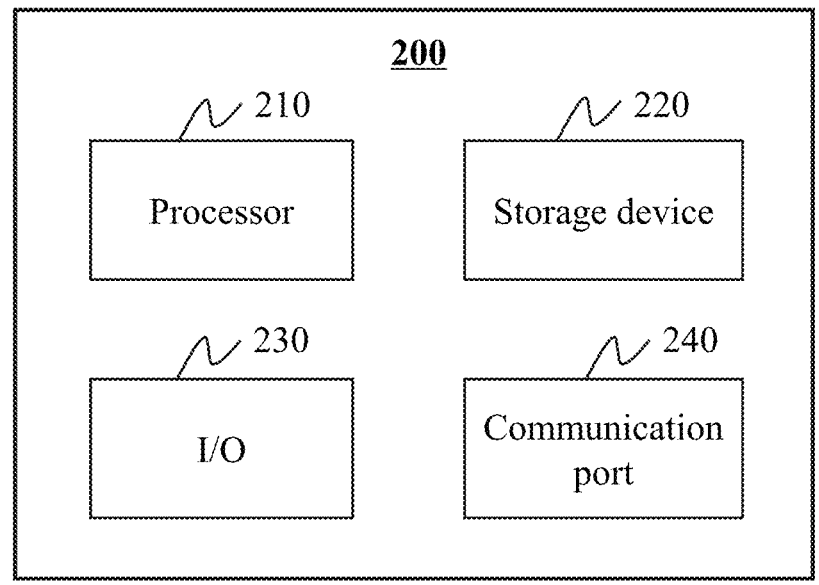
FIG. 2 is a schematic diagram illustrating an exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a second image, or a first image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

Provided herein are systems and components for non-invasive imaging and/or treatment, such as for disease diagnosis, treatment or research purposes. In some embodiments, the systems may include a radiotherapy (RT) system, a computed tomography (CT) system, an emission computed tomography (ECT) system, an X-ray photography system, a positron emission tomography (PET) system, a magnetic resonance imaging (MRI) system, or the like, or any combination thereof. For illustration purposes, the disclosure describes systems and methods for radiotherapy. The term "image" used in this disclosure may refer to a 2D image, a 3D image, or a 4D image. In some embodiments, the term "image" may refer to an image of a region, e.g., a region of interest (ROI), of a patient. The term "region of interest" or "ROI" used in this disclosure may refer to a part of an image along a line, in two spatial dimensions, in three spatial dimensions, or any of the proceeding as they evolve as a function of time. The image may be an Electronic Portal Imaging Device (EPID) image, a CT image, a fluoroscopy image, an ultrasound image, a PET image, or an MR image. This is not intended to limit the scope of the present disclosure. For persons having ordinary skills in the art, a certain number of variations, changes, and/or modifications may be deduced under the guidance of the present disclosure. Those variations, changes, and/or modifications do not depart from the scope of the present disclosure.

An aspect of the present disclosure relates to an RT system. The RT system may obtain a treatment plan, a planning image, and one or more treatment images of a subject, determine primary images of the subject based on the one or more treatment images, and determine inversely-attenuated primary images of the subject by inversely attenuating the primary images to a plane located between the subject and a collimator assembly of the radiation device. A projection image of the patient may generally be formed by both unscattered primary radiation passing through the patient, and scatter component due to radiation scatter within the patient. The term "primary image" refers to the component of the image created by the primary radiation. Typically, the estimated primary image may be determined by removing estimated scatter component contribution from an image. The RT system may further determine a dose delivered to the subject and estimate machine parameters of the radiation device corresponding to the inversely-attenuated primary images. To determine the inversely-attenuated primary images of the subject, a penumbra model characterizing penumbra characteristics (e.g., a width of a penumbra region) regarding edges of a treatment field defined by the collimator assembly. Based on the penumbra model, the accuracy of the inversely-attenuated primary images may be improved, an actual dose delivered to the subject may be estimated, and machine parameters corresponding to a planned radiation dose may be obtained.

Figure 1:
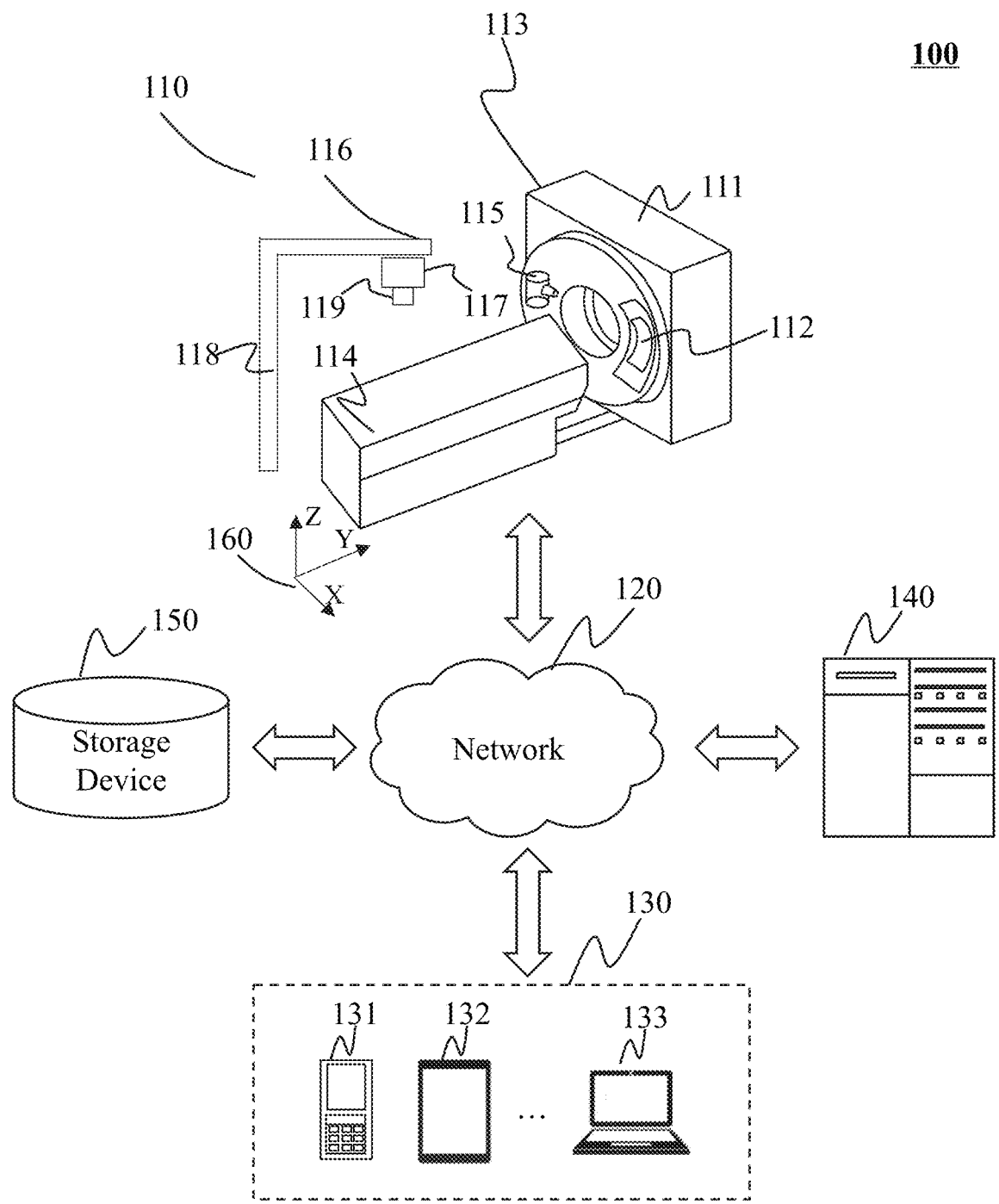
FIG. 1 is a schematic diagram illustrating an exemplary radiotherapy (RT) system according to some embodiments of the present disclosure.

FIG. 1 is a schematic diagram illustrating an exemplary RT system 100 according to some embodiments of the present disclosure. The RT system 100 may include an RT device 110, a network 120, one or more terminals 130, a processing device 140, and a storage device 150. In some embodiments, two or more components of the RT system 100 may be connected to and/or communicate with each other via a wireless connection (e.g., the network 120), a wired connection, or a combination thereof. The connection between the components of the RT system 100 may be variable. Merely by way of example, the RT device 110 may be connected to the processing device 140 through the network 120 or directly. As a further example, the storage device 150 may be connected to the processing device 140 through the network 120 or directly.

The RT device 110 may be configured to deliver a radiotherapy dose to a subject. For example, the treatment device may deliver one or more radiation beams to a treatment region (e.g., a tumor) of a subject for causing an alleviation of the subject's symptom. A radiation beam may include a plurality of radiation beamlets. In the present disclosure, "subject" and "object" are used interchangeably. The subject may include any biological subject (e.g., a human being, an animal, a plant, or a portion thereof) and/or a non-biological subject (e.g., a phantom). For example, the subject may include a specific portion of a body, such as the head, the thorax, the abdomen, or the like, or a combination thereof, of the subject. In some embodiments, the treatment device may be an image-guided radiation therapy (IGRT) device, a conformal radiation therapy device, an intensity-modulated radiation therapy (IMRT) device, an intensity-modulated arc therapy (IMAT) device, an emission guided radiation therapy (EGRT), or the like.

In some embodiments, the RT device 110 may be an IGRT device configured to acquire image data relating to the subject, and perform a radiotherapy treatment on the subject. For example, as illustrated in FIG. 1, the RT device 110 may include an imaging component 113, a treatment component 116, a table (or referred to as couch) 114, or the like. The imaging component 113 may be configured to acquire an image of the subject before radiotherapy treatment, during the radiotherapy treatment, and/or after the radiotherapy treatment. In some embodiments, the imaging component 113 may include a computed tomography (CT) device (e.g., a cone beam CT (CBCT) device, a fan beam CT (FBCT) device, a multi-slice CT (MSCT) device, etc.), a magnetic resonance imaging (MRI) device, an ultrasound imaging device, a fluoroscopy imaging device, a single-photon emission computed tomography (SPECT) device, a positron emission tomography (PET) device, an X-ray imaging device, or the like, or any combination thereof.

In some embodiments, the imaging component 113 may include an imaging radiation source 115, a detector 112, a gantry 111, or the like. The imaging radiation source 115 and the detector 112 may be mounted on the gantry 111. The imaging radiation source 115 may emit radioactive rays to the subject. The detector 112 may detect radiation events (e.g., x-ray photons, gamma-ray photons) emitted from the imaging region of the imaging component 113. In some embodiments, the detector 112 may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The treatment component 116 may be configured to deliver radiation doses to the subject. The treatment component 116 may include a treatment radiation source 117, a gantry 118, and a collimator assembly 119. The treatment radiation source 117 may be configured to emit treatment radiations towards the subject. In some embodiments, the treatment radiation source 117 may include a linear accelerator (LINAC). The collimator assembly 119 may be configured to control the shape of the treatment radiations generated by the treatment radiation source 117.

In some embodiments, the imaging component 113 may be spaced by a distance from the treatment component 116. In some embodiments, rotation axes of the gantry 111 of the imaging component 113 and the gantry 118 of the treatment component 116 may be the same or different. The subject may be positioned in different positions on the table 114 for imaging and treatment. In some embodiments, the imaging radiation source 115 and the treatment radiation source 117 may be integrated as one radiation source to image and/or treat the subject. In some embodiments, the imaging component 113 and the treatment component 116 may share the same gantry. For example, the treatment radiation source 117 may be mounted on the gantry 111 of the imaging component 113. A subject may be placed on the table 114 for treatment and/or imaging.

The couch 114 may be configured to support the subject to be treated and/or imaged. In some embodiments, the couch 114 may be movable between the treatment component 116 and the imaging component 113 along a Y-axis direction of a coordinate system 160 as shown in FIG. 1. In some embodiments, the couch 114 may be configured to rotate and/or translate along different directions to move the subject to a desired position (e.g., an imaging position under the imaging component 113 for imaging, a treatment position under the treatment component 116 for treatment, etc.).

The network 120 may include any suitable network that can facilitate the exchange of information and/or data for the RT system 100. In some embodiments, one or more components (e.g., the RT device 110, the terminal(s) 130, the processing device 140, the storage device 150, etc.) of the RT system 100 may communicate information and/or data with one or more other components of the RT system 100 via the network 120. For example, the processing device 140 may obtain image data from the RT device 110 via the network 120. As another example, the processing device 140 may obtain user (e.g., a doctor, a radiologist) instructions from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
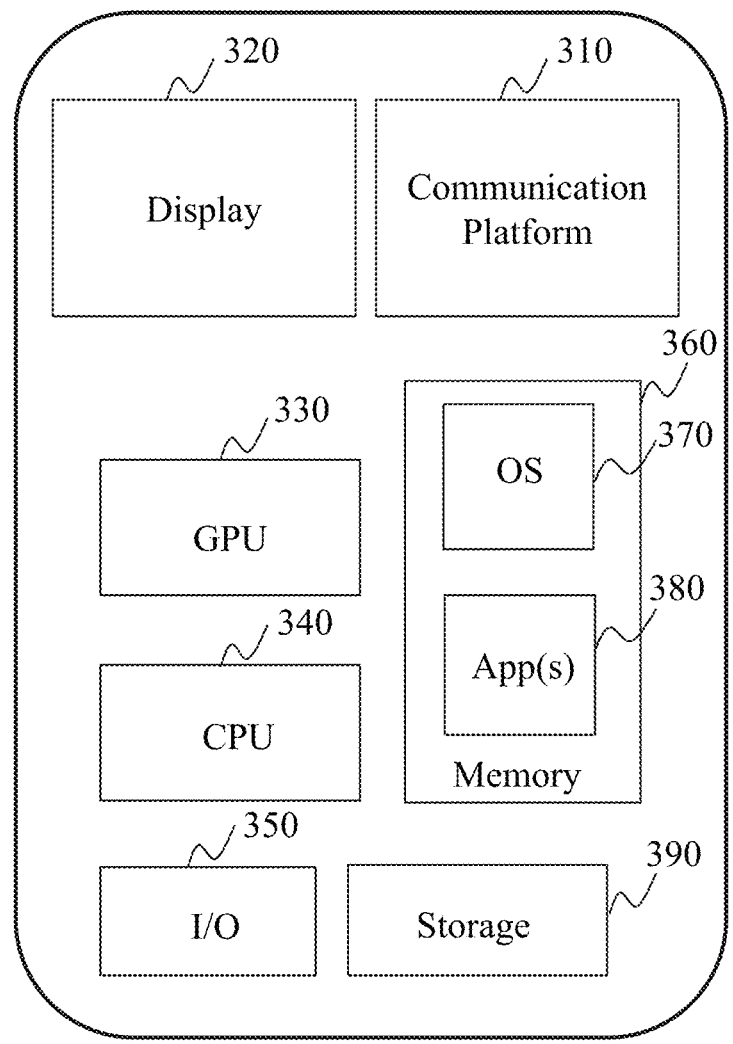
FIG. 3 is a schematic diagram illustrating hardware and/or software components of an exemplary mobile device according to some embodiments of the present disclosure.

The terminal(s) 130 may enable user interaction between a user and the RT system 100. In some embodiments, the terminal(s) 130 may be connected to and/or communicate with the RT device 110, the processing device 140, and/or the storage device 150. For example, the terminal(s) 130 may display a treatment image of the subject obtained from the processing device 140. In some embodiments, the terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process information obtained from the RT device 110, the terminal(s) 130, and/or the storage device 150. For example, the processing device 140 may obtain one or more treatment images of a subject form one or more components (e.g., the RT device 110 (e.g., the imaging component 113), the terminal(s) 130, the storage device 150) of the RT system 100. The processing device 140 may convert the one or more treatment images into primary images (typically estimates thereof, by removing the estimated scatter contribution), and determine inverse-attenuated primary images of the subject by inverse attenuating the primary images to a plane between the subject and a collimator assembly of the treatment radiation source 117 of the RT device 110. Further, the processing device 140 may determine an estimate of dose delivered to the subject based at least in part on the inverse-attenuated primary images.

In some embodiments, the processing device 140 may be a single server or a server group. The server group may be centralized or distributed. In some embodiments, the processing device 140 may be local or remote. For example, the processing device 140 may access information stored in the RT device 110, the terminal(s) 130, and/or the storage device 150 via the network 120. As another example, the processing device 140 may be directly connected to the RT device 110, the terminal(s) 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the RT device 110, the terminal(s) 130, and/or the processing device 140. For example, the storage device 150 may store scan data, treatment images, a treatment plan, etc., of the subject. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components (e.g., the RT device 110, the processing device 140, the terminal(s) 130) of the RT system 100. One or more components of the RT system 100 may access the data and/or instructions stored in the storage device 150 via the network 120. In some embodiments, the storage device 150 may be directly connected to or communicate with one or more other components (e.g., the RT device 110, the processing device 140, the terminal(s) 130) of the RT system 100. In some embodiments, the storage device 150 may be part of the processing device 140.

For illustration purposes, a coordinate system 160 is provided in FIG. 1. The coordinate system 160 may be a Cartesian system including an X-axis, the Y-axis, and a Z-axis. The X-axis and the Y-axis shown in FIG. 1 may be horizontal, and the Z-axis may be vertical. As illustrated, the positive X direction along the X-axis may be from the left side to the right side of the table 114 viewed from the direction facing the front of the RT device 110; the positive Y direction along the Y-axis shown in FIG. 1 may be from the end to the head of the table 114; the positive Z direction along the Z-axis shown in FIG. 1 may be from the lower part to the upper part of the RT device 110.

It should be noted that the above description regarding the RT system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the RT system 100 may include one or more additional components and/or one or more components of the RT system 100 described above may be omitted. In some embodiments, a component of the RT system 100 may be implemented on two or more sub-components. Two or more components of the RT system 100 may be integrated into a single component. For example, the treatment component 116 in the RT device 110 may be integrated into the imaging component 113.

In some embodiments, radiation dosimetry methods disclosed herein may be implemented on a single-modality RT system, which may include an RT device (e.g., a same or similar device as the treatment component 116), the network 120, the storage device 150, the processing device 140, the terminal(s) 130, or the like, or any combination thereof. For illustration purposes, the implementation of the radiation dosimetry methods on the RT system 100 is described hereinafter, and this is not intended to be limiting.

FIG. 2 is a schematic diagram illustrating exemplary hardware and/or software components of a computing device 200 according to some embodiments of the present disclosure. The computing device 200 may be used to implement any component of the RT system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the RT system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 140 in accordance with techniques described herein. The computer instructions may include, for example, routines, programs, subjects, components, data structures, procedures, modules, and functions, which perform particular functions described herein. For example, the processor 210 may process image data obtained from the RT device 110, the terminal(s) 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data obtained from one or more components of the RT system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure. For example, the storage device 220 may store a program to be executed by the processing device 140 to estimate a radiation dose delivered to the subject. As another example, the storage device 220 may store a program to be executed by the processing device 140 to cause the treatment radiation source 117 to adjust its machine parameters including, for example, positions of jaws.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the RT device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 according to some embodiments of the present disclosure. In some embodiments, one or more terminals 130 and/or a processing device 140 may be implemented on a mobile device 300, respectively.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
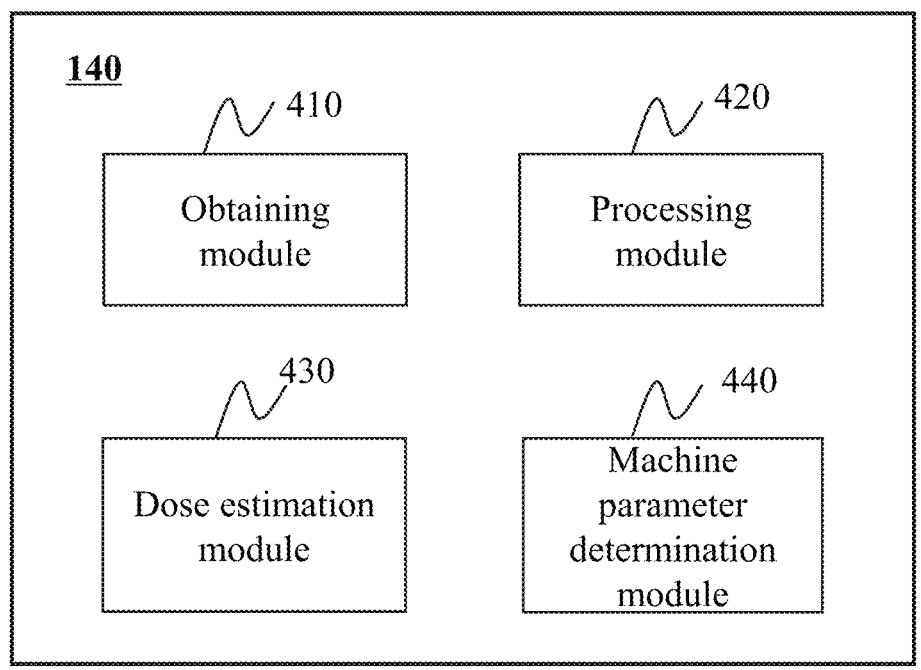
FIG. 4 is a block diagram illustrating an exemplary processing device according to some embodiments of the present disclosure.

FIG. 4 is a block diagram illustrating an exemplary processing device 140 according to some embodiments of the present disclosure. As shown in FIG. 4, the processing device 140 may include an obtaining module 410, a processing module 420, a dose estimation module 430, and a machine parameter determination module 440.

The obtaining module 410 may obtain data and/or information. The obtaining module 410 may obtain data and/or information from the RT device 110, the terminal(s) 130, the processing device 140, the storage device 150, or any devices or components capable of storing data via the network 120. For example, the obtaining module 410 may obtain data and/or information from a medical cloud data center (not shown) via the network 150. The obtained data and/or information may include a treatment plan of a subject, a planning image of the subject, one or more treatment image of the subject, user instructions, algorithms, parameters (e.g., parameters of the RT device 110), program codes, information of a subject, or the like, or a combination thereof. In some embodiments, the obtaining module 510 may obtain a treatment plan, a planning image, and one or more treatment image of the subject. In some embodiments, the obtaining module 510 may transmit the obtained data and/or information to a computing device (including, for example, the processing module 420, the dose estimation module 430, the machine parameter determination module 440, etc.) for processing.

The processing module 420 may process the obtained data/information. In some embodiments, the processing module 420 may determine primary images of the subject based on the one or more treatment images. The primary images may be obtained by removing scatter component of radiation from the one or more treatment images. In some embodiments, the primary images may be determined by performing a scatter correction on the treatment images. In some embodiments, the processing module 420 may further determine inversely-attenuated primary images of the subject by inversely attenuating the primary images to a plane between the subject and a collimator assembly of the radiation device (e.g., the treatment component 116 of the RT device 110) emitting the radiation on the basis of which the primary images are determined. The one or more primary images may be inversely attenuated to the plane using at least one volumetric image of the subject. The at least one volumetric image of the subject may include a representation of anatomical structures in the volume of the subject. Exemplary volumetric images may include a CT image, an MR image, an ultrasound image, or the like, or any combination thereof. In some embodiments, the at least one volumetric image may be or include the planning image. In some embodiments, the at least one volumetric image may be or include at least one of the one or more treatment images.

The dose estimation module 430 may estimate a dose delivered to the subject based on the inversely-attenuated primary images of the subject. The dose estimation module 430 may determine an input fluence map based on the inversely-attenuated primary images of the subject. The input fluence map may represent the amount of radiation passing through a spatial region. In some embodiments, the input fluence map determined based on the inversely-attenuated primary images of the subject may be presented in the form of a matrix that covers a spatial region (e.g., the input fluence plane). For each point in the input fluence plane, the input fluence map may define the amount of radiation passing through the point. The dose estimation module 430 may estimate the dose delivered to the subject by inputting the input fluence map into a forward dose calculation algorithm.

The machine parameter determination module 440 may estimate machine parameters of the radiation device corresponding to the inversely-attenuated primary images. The machine parameters of the radiation device (e.g., the RT device) may include, for example, positions of a gantry of the radiation device (e.g., the gantry 118 of the treatment component 116), a shape of the collimator assembly of the radiation device (e.g., the RT device 110), a geometry and/or position of at least one element of the collimator assembly, or the like, or any combination thereof. In some embodiments, the machine parameter determination module 440 may determine the machine parameters of the radiation device according to an optimazation function. Solutions of the optimazation function may be used to estimate the machine parameters by iteratively synthesizing images for vectors of different values of machine parameters with the objective of minimizing a discrepancy between input radiation estimated from a synthetic image and a treatment image. In some embodiments, a plurality of iterations may be performed for reducing the discrepancy.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. For example, the processing device 140 may also include a transmission module configured to transmit signals (e.g., electrical signals, electromagnetic signals) to one or more components (e.g., the RT device 110, the terminal(s) 130, the storage device 150) of the RT system 100. As a further example, the processing device 140 may include a storage module (not shown) used to store information and/or data (e.g., a treatment plan, treatment images, processing results, etc.) associated with the radiation dosimetry. Additionally or alternatively, two or more modules may be integrated into a single module and/or a module may be divided into two or more units. For example, the dose estimation module 430, a machine parameter determination module 440 may be combined into the processing module 420 which may further estimate radiation doses delivered to the subject and determine machine parameters corresponding to a planned radiation dose. However, those variations and modifications also fall within the scope of the present disclosure.

Figure 5:
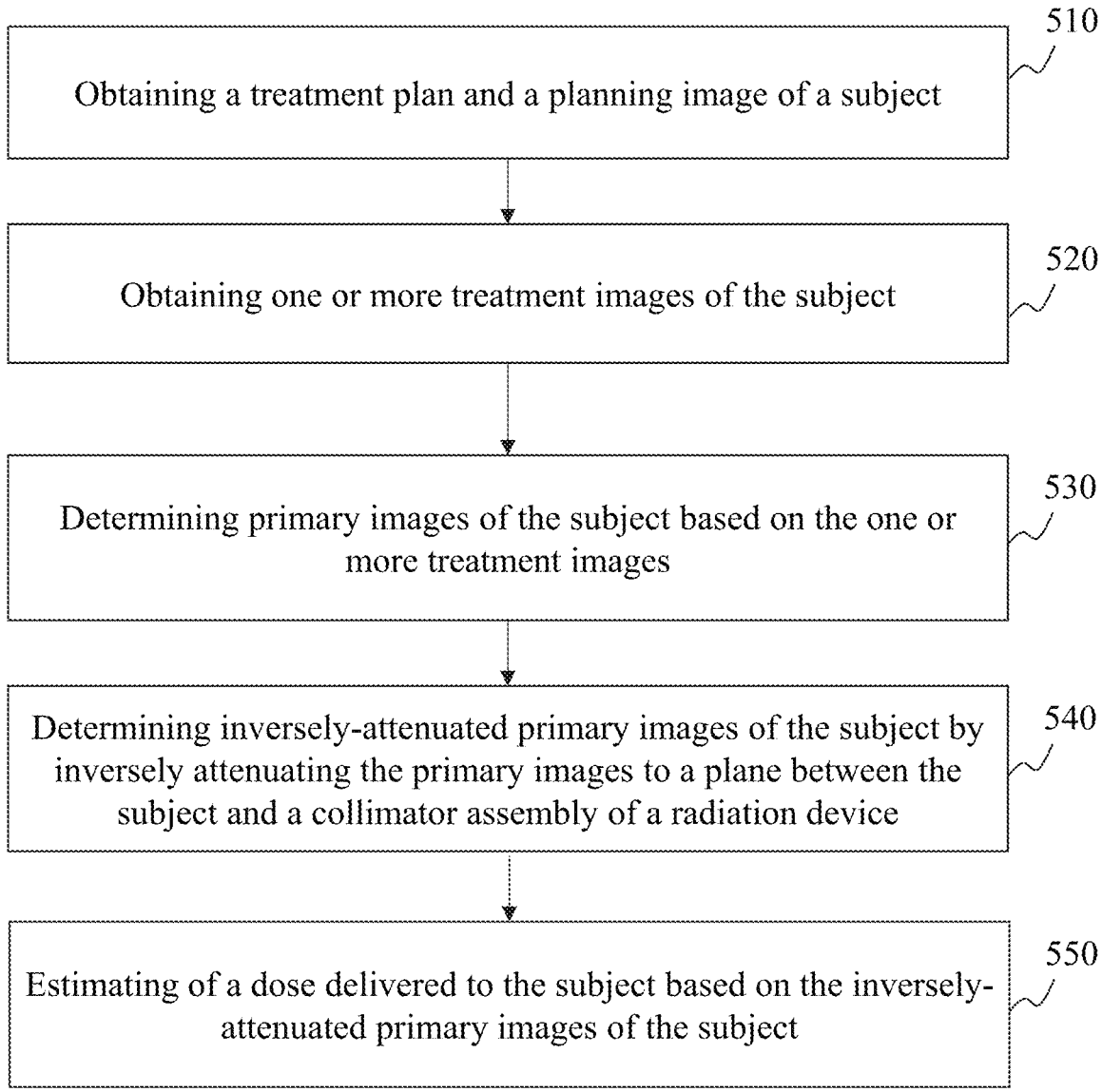
FIG. 5 includes a flowchart illustrating an exemplary process for determining an estimate of a dose delivered to the subject according to some embodiments of the present disclosure.

FIG. 5 includes a flowchart illustrating an exemplary process for determining an estimate of a dose delivered to the subject according to some embodiments of the present disclosure. In some embodiments, process 500 may be executed by the RT system 100. For example, the process 500 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 500.

In 510, the processing device 140 (e.g., the obtaining module 410) may obtain a treatment plan and a planning image of a subject.

The subject may include a biological subject (e.g., a human, an animal), a non-biological subject (e.g., a phantom), or the like, or a combination thereof. For example, the subject may include a patient. As another example, the subject may include a specific portion, such as the chest, a breast, and/or the abdomen of the patient.

The planning image may refer to an image of the subject according to which a treatment plan is made. The planning image may be used to identify and locate one or more radiation targets of the subject. A radiation target may be an anatomical structure, such as an organ, tissue, a blood vessel, or the like, or a combination thereof, of the subject. The planning image may be generated in a planning stage of a radiation treatment. For example, before the radiotherapy treatment (e.g., days or weeks before the treatment commences) is performed on the subject, the planning image of the subject may be acquired using an imaging device (e.g., the imaging component 113 of the RT device 110, or an imaging device other than the imaging component 113).

In some embodiments, the planning image may include a two-dimensional (2D) image, a three-dimensional (3D) image, etc. The planning image may be a CT image, an EPID image, a fluoroscopy image, an ultrasound image, a PET image, a SPECT image, an MR image, etc. In some embodiments, the planning image may be a CT image generated by scanning the subject using a CT scanner. In some embodiments, the CT scanner may be a CBCT scanner and/or an MSCT scanner. The CBCT scanner may perform a CBCT scan of a subject. The MSCT scanner may perform an MSCT scan of a subject. The images generated based on the CBCT scan or the MSCT scan may be stored in a storage device (e.g., the storage device 150, the storage device 220, or an external storage device) associated with the RT system 100 for radiation therapy planning.

In some embodiments, after the planning image of the subject is generated, the RT system 100 may store the planning image in a storage device (e.g., the storage device 150, the storage device 220, or an external storage device) associated with the RT system 100 for radiation therapy planning. The processing device 140 may obtain the planning image from the storage device if needed. After the planning image of the subject is obtained, a treatment plan may be designed for the subject based on the planning image.

The treatment plan may describe at least one radiation field (also referred to as treatment field) to be applied to the subject. Each treatment field may be associated with a radiation output quantity, such as a number (or count) of delivery system radiation output monitor units (MUs) and an MU-rate (MU per unit time) associated with the field. The treatment plan may be made before a radiation treatment is applied to the subject. The radiation treatment may be a photon-based radiation therapy, a brachytherapy, an electron beam therapy, a proton therapy, a neutron therapy, or the like, or any combination thereof.

The treatment plan may include one or more treatment fractions. For each of the one or more treatment fractions, the treatment plan may include a plurality of treatment parameters, such as a planned fraction duration, a planned radiation dose, a planned radiation energy delivery direction, a planned beam shape of a radiation beam, a planned cross-sectional area of the radiation beam, a planned region of interest (ROI) (e.g., the radiation target in the subject), etc. For example, the treatment plan may provide a total dose (e.g., 0.1 Gy, 10 Gy, 50 Gy, 100 Gy, etc.) and a dose distribution within a radiation target. In some embodiments, the treatment plan may be made based on the planning image. For example, tissue attenuation values of the subject may be estimated based on the planning image. The estimated tissue attenuation values may be converted to electron densities and used to estimate the planned radiation dose to be applied on the radiation target.

In 520, the processing device 140 (e.g., the obtaining module 410) may obtain one or more treatment images of the subject.

A treatment image may also be referred to as a measured image. In some embodiments, the one or more treatment images of the subject may be obtained from a storage device (e.g., the storage device 150, the storage device 220, or an external storage device) associated with the RT system 100. In some embodiments, the one or more treatment images may be generated by performing at least a portion of the treatment plan using a radiation device (e.g., the RT device 110) during at least one (e.g., each) of the one or more treatment fractions. During a treatment fraction, at least a radiation beam may be delivered towards the subject (e.g., the radiation target). The radiation beam may include a beam of particle rays or photon rays. Exemplary particle rays may include neutron, proton, electron, p-meson, heavy ion, a-ray, or the like, or any combination thereof. Exemplary photon rays may include X-ray, y-ray, ultraviolet, laser, or the like, or any combination thereof.

In some embodiments, scanning data from one or more scans of the subject may be acquired. In some embodiments, a scan may be performed on the subject during each of one or more of the treatment fractions. The one or more treatment images may be generated based on the acquired scanning data.

In some embodiments, the one or more treatment images may be EPID images. The EPID images may be generated by an EPID. The EPID may be positioned in the pathway of a radiation beam in a radiation treatment. The EPID images may be generated based on energy deposited in the EPID. In some embodiments, the deposited energy may be measured in the pixel level of the EPID.

In 530, the processing device 140 (e.g., the processing module 420) may determine primary images of the subject based on the one or more treatment images.

In some embodiments, during a treatment, radiation deposited in the subject may include primary radiation and scattered radiation. The primary radiation may also be referred to a primary component of the radiation. The scattered radiation may also be referred to as a scatter component of the radiation. The primary images may be obtained by removing the scatter component from the one or more treatment images. In some embodiments, the primary images may be determined by performing a scatter correction on the treatment images. Exemplary scatter correction techniques may include a convolution technique, a deconvolution technique, an ordered subsets convex technique, a beam-stop measurement technique, or the like, or any combination thereof.

In some embodiments, the primary images may be determined by subtracting the scatter component from the one or more treatment images. In some embodiments, the scatter component may be estimated according to a scatter simulation technique or algorithm, such as a Monte Carlo (MC) simulation, a kernel-based algorithm, a scatter-to-primary ratio (SPR), etc. For example, the scatter component may be estimated using the MC simulation or using Boltzmann transit calculations (or an approximation thereof) based on the treatment plan, a beam model, and a detector model. After the scatter component is determined, the primary images may be determined by subtracting the scatter component from the one or more treatment images. Alternatively, the primary component may be obtained by dividing the measured image by (1+SPR), where SPR is the ratio of the estimated scatter component to the estimated primary component.

In 540, the processing device 140 (e.g., the processing module 420) may determine inversely-attenuated primary images of the subject by inversely attenuating the primary images to a plane between the subject and a collimator assembly of the radiation device (e.g., the treatment component 116 of the RT device 110) emitting the radiation on the basis of which the primary images are determined.

The collimator assembly of the radiation device (e.g., the collimator assembly of the treatment component 116 of the RT device 110) may shape the radiation beam emitted to the subject, thus defining a shape of a treatment field. The collimator assembly of the radiation device may include a plurality of elements, such as a multi-leaf collimator (MLC), at least one jaw, or the like, or a combination of thereof. Different positions and shapes of elements of the collimator assembly (e.g., the leaves of the MLC and the at least one jaw) may form a treatment field of different shapes. For example, if the elements of the collimator assembly form an aperture having the shape of a circle, the treatment field may have the shape of a circle or roughly a circle.

In some embodiments, the collimator assembly of the radiation device may include a multi-leaf collimator (MLC) situated in an MLC plane and at least one jaw situated in a jaw plane other than the MLC plane. The MLC may include at least one first group of leaves and at least one second group of leaves opposing each other and being moveable to form an aperture corresponding to a treatment field by blocking pathways of a first portion of the radiation beam within a treatment field. In some embodiments, the MLC may be a multi-layer MLC. The multi-layer MLC may be comprised of several layers separated substantially along the beam direction. A second portion of the radiation beam may impinge on a radiation target or a portion thereof located in the treatment field. In some embodiments, a gap may exist between the projection of the at least one jaw along a direction of the radiation beam and the treatment field. The at least one jaw may shield or block a part of the first portion of radiation beam. The MLC and/or the at least one jaw may be made of a radiation-impermeable material. Exemplary radiation-impermeable materials may include tungsten, lead, steel, or the like, or an alloy thereof, or a combination thereof. In some embodiments, a projection of the at least one jaw along the direction of the radiation beam may partially overlap the treatment field, i.e., forming an aperture corresponding to the treatment field together with the MLC, thereby improving the accuracy and adjustability of the treatment field.

The plane to which the inversely-attenuated primary images of the subject are projected may be located between the subject and the collimator assembly (e.g., the collimator assembly 119). Since input fluence of the radiation beam in the plane is estimated, the plane may also be referred to as input fluence plane. In some embodiments, the input fluence plane may be parallel or substantially parallel to the MLC plane in which the MLC is situated and/or the jaw plane in which the at least one jaw is situated. The MLC plane and the jaw plane may be (substantially) parallel to each other. The MLC plane and/or the jaw plane may be (substantially) perpendicular to the direction in which the radiation beam travels from the radiation device (e.g., the treatment component 116 of the RT device 110) to the subject. In some embodiments, the input fluence plane may be located between the subject and one of the MLC plane and the jaw plane which is closer to the patient than the other. For example, the input fluence plane may be located between the subject and the MLC plane if the MLC plane is closer to the subject than the jaw plane. Accordingly, along the direction from the radiation device (e.g., the treatment component 116 of the RT device 110) to the subject, the input fluence plane may be located between the MLC plane and the subject, while the jaw plane may be upstream to the input fluence plane.

In some embodiments, the input fluence plane may be located by a particular distance from the subject (e.g., a center or an upper edge of an outline of a cross section of the subject in the X-Z plane with reference to the coordinate system 160 as illustrated in FIG. 1). In some embodiments, the input fluence plane may be close to the subject. For example, the input fluence plane may be located from the subject by a particular distance of 20 centimeters, 30 centimeters, 40 centimeters, 50 centimeters, etc. In some embodiments, the distance may be determined by a user (e.g., a technician, a doctor, etc.), according to default settings of the RT system 100, etc. In some embodiments, the distance between the input fluence plane and the subject may relate to basic information, such as the age, the weight, the height, the head-circumference, the chest-circumference, the thickness of the body, etc., of the subject.

The one or more primary images may be inversely attenuated to the plane using at least one volumetric image of the subject. The at least one volumetric image of the subject may include a representation of anatomical structures in the volume of the subject. Exemplary volumetric images may include a CT image, an MR image, an ultrasound image, or the like, or any combination thereof. In some embodiments, the at least one volumetric image may be or include the planning image. In some embodiments, the at least one volumetric image may be or include at least one of the one or more treatment images.

In actual situations, the treatment field may be surrounded by a penumbra region and an umbra region. An umbra region may be a region in which the radiation beam is completely obscured by the collimator assembly (e.g., at least one collimator element). The penumbra region may be a region in which a portion of the radiation beam is obscured by the collimator assembly. The penumbra region may distribute along one or more edges the treatment field (also referred to as field edges), forming a transition between the treatment field and the umbra region. The penumbra region may have a width of at each point (e.g., a pixel, a voxel) along the field edges. In some embodiments, a width of the penumbra region may be defined as a distance along which an in-field value (e.g., a relative dose) of the edge of the treatment field transitions from 80% to 20% or from 20% to 80%. In some embodiments, the width of the penumbra region may vary along the field edges.

In some embodiments, the treatment field may be shown in one or more images (e.g., a treatment image, such as an EPID image) of the subject. The sharpness of the field edges in the one or more images may relate to the width of the penumbra region. In some embodiments, the sharpness of the field edges may dependent on, for example, a geometry and position of at least one element of the collimator assembly, scattering of the radiation beam that occurs within the subject, or the like, or a combination thereof. The geometry of the at least one element of the collimator assembly may include a shape of each leaf of the MLC and/or each jaw of the at least one jaw, a thickness of each leaf of the MLC and/or each jaw of the at least one jaw, a chamfering/shape (e.g., round, flat, etc.) of an end of each leaf of the MLC and/or each jaw of the at least one jaw, etc. Generally, due to the scattering of the radiation beam within the subject, a radiation ray in the radiation beam that traverses a thicker anatomy of the subject may correspond to a blurrier edge of the treatment field, thus leading to a wider penumbra region and a lower contrast between the treatment field and the umbra region.

Figure 6:
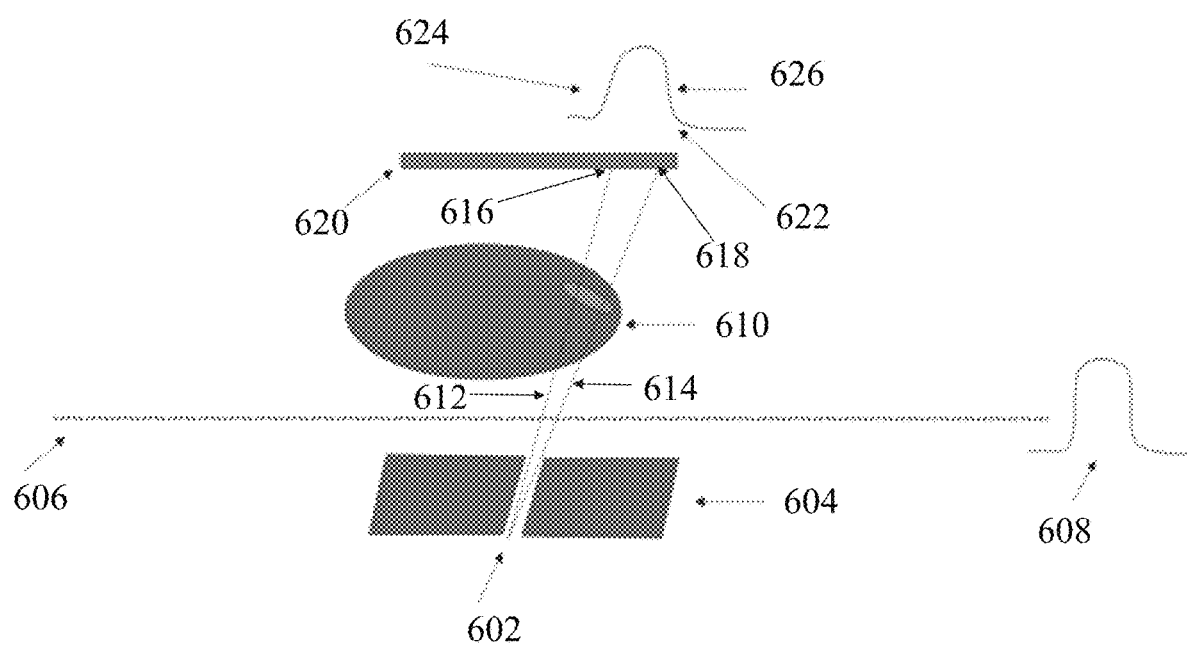
FIG. 6 illustrates an exemplary relationship between widths of a penumbra region at field edges of a treatment field and pathlengths of a corresponding radiation beam through a subject according to some embodiments of the present disclosure.

FIG. 6 illustrates an exemplary relationship between widths of a penumbra region at field edges of a treatment field and pathlengths of a corresponding radiation beam through a subject according to some embodiments of the present disclosure. A radiation beam generated by a radiation source 602 may be shaped by a collimator assembly 604, and emit toward a subject 610. As shown in FIG. 6, radiation rays in different directions of the radiation beam may traverse anatomical structures of different thicknesses and/or different material compositions within the subject 610. Radiation rays such as a ray 612 may traverse longer (actual or effective) paths within the subject, and radiation rays such as a ray 614 may traverse shorter paths within the subject. The length of a path that a ray 612 traverses within a subject may be assessed in terms of a medium-equivalent thickness of one type of medium, or a combination of medium-equivalent thicknesses of multiple types of media, as described elsewhere in the present disclosure. See, e.g., FIGS. 7A and 7B, and relevant description thereof. The radiation rays that traverse the subject 610 may be detected by the detector (e.g., an EPID) 620, and an intensity profile 622 representing intensities of the detected radiation rays may be generated.

The intensity profile 622 may have a shape of an arch including a ramp-up side 624 in a left portion of the intensity profile 622 and a ramp-down side 626 in a right portion of the intensity profile 622. The ramp-up side 624 may correspond to the ray 612, which has traversed a longer path within the subject, and the ramp-down side 626 may correspond to the ray 614, which has traversed a shorter path within the subject. According to the intensity profile 622, the ramp-up side 624 may have a smaller steepness (i.e., a smoother transition of the amplitude of the intensity profile 622). Thus, a distance along which an in-field value of an edge 616 of the treatment field transitions by a specific amount, e.g., from 20% to 80%, may be longer, and a corresponding width of the penumbra region may be larger. Conversely, the ramp-down side 626 may have a larger steepness (i.e., a shaper transition of the amplitude of the intensity profile 622). Thus, a distance along which an in-field value of an edge 618 of the treatment field transitions by the same amount, e.g., from 80% to 20% may be shorter, and a corresponding width of the penumbra region may be smaller.

An true intensity profile 608 representing true intensities of incident radiation rays at a plane 606 onto which the primary images are inversely attenuated may be provided. According to the true intensity profile 608, a ramp-up side in a left portion of the true intensity profile 608 and a ramp-down side in a right portion of the true intensity profile 608 may be substantially symmetric. Thus, it may be inferred that radiation rays such as the ray 612 that have traversed longer paths within the subject may be associated with a wider penumbra region, and radiation rays such as the ray 614 that have traversed short paths within the subject may be associated with a narrower penumbra region.

Since the penumbra region along the field edges relates to factors including, such as, e.g., the geometry and position of at least one element of the collimator, scattering of the radiation beam that occurs within the subject, etc., the effect of the penumbra region may need to be quantified so as to obtain accurate inversely-attenuated primary images, especially, around the field edges.

In some embodiments, penumbra characteristics regarding edges of one or more elements of the collimator assembly may be determined. The penumbra characteristics regarding edges of the one or more elements of the collimator assembly may refer to characteristics of the penumbra region at edges of a treatment field, which corresponds to edges of one or more elements of the collimator assembly (the edges of one or more elements of the collimator assembly may contribute to the field edges). The characteristics of the penumbra region may include, for example, widths of the penumbra region.

The processing device 140 may determine the penumbra characteristics regarding the edges of the one or more elements of the collimator assembly (also referred to as penumbra characteristics regarding the edges of the collimator assembly) using various techniques or algorithms. In some embodiments, the penumbra characteristics regarding edges of the collimator assembly may be determined based on a forward transport of the treatment field through the subject (also referred to as forward transport simulation for brevity). The forward transport simulation may simulate transport of particles of a particle ray or ray beam or photons of a photon ray or ray beam through the subject in a direction from the radiation source to the detector. The forward transport simulation may be implemented based on techniques or algorithms of various types. In some embodiments, the forward transport simulation may be implemented by an MC simulation, a Boltzmann transport algorithm, or the like, or a combination thereof. In some embodiments, the forward transport simulation may include other simulation algorithms, such as Compton scatter modeling.

In some embodiments, particles or photons with high energy levels may traverse at least one element of the collimator assembly (e.g., at least one leaf of the MLC and/or at least one jaw) in a thickness direction of the at least one element, which may be referred to as a collimator penetration effect. The particles or photons that traverse the at least one element of the collimator assembly may enter a planned umbra region (that is supposed to be an umbra region) and/or a penumbra region, traverse anatomical structures of the subject in the umbra region and/or the penumbra region, and be detected by a detector. In this case, a background of the image of the subject may be increased, and a contrast between the treatment field and the umbra region may be reduced accordingly. In some embodiments, the collimator penetration effect may be simulated in the forward transport of the treatment field through the subject. In some embodiments, scattering of particles or photons in the subject may also be simulated in the forward transport of the treatment field through the subject. For example, the scattering may be estimated according to a scatter-to-primary ratio (SPR) algorithm, the MC simulation, etc.

In some embodiments, the forward transport of the treatment field through the subject may be associated with particular positions of at least one element of the collimator assembly. In some embodiments, the particular positions of the at least one element of the collimator assembly may be in a certain range (e.g., a perturbation range). Merely by way of example, the particular positions may be positions perturbed or deviated from at least one planned position with a perturbation amplitude. In some embodiments, the at least one planned position and/or the perturbation amplitude may be determined by a user (e.g., a technician, a doctor, etc.), according to default settings of the RT system 100, etc. In some embodiments, the at least one planned position and/or the perturbation amplitude may be configured such that a range of the penumbra region corresponding to the particular positions may cover a certain range of ambiguity around the field edges in a detected image.

In some embodiments, the penumbra characteristics regarding the edges of the collimator assembly may be determined based on a simplified forward transport simulation. In some embodiments, the simplified forward transport simulation may be similar to or the same as the forward transport simulation exemplified above except that scatter estimation in the simplified forward transport simulation may be simplified. In some embodiments, the scatter estimation in the simplified forward transport simulation may be implemented by a kernel based algorithm. Exemplary kernel based algorithms may include scatter kernel superposition (SKS), adaptive scatter kernel superposition (ASKS), fast adaptive scatter kernel superposition (fASKS), SKS with asymmetric kernels, or the like, or any combination thereof. In some embodiments, nonstationary kernels may be used in the kernel based algorithm so as to approximate scatter transport in practical applications. Merely by way of example, the shapes of the kernels in the kernel based algorithm may be adapted according to local thickness (e.g., water-equivalent thickness (WET)) for radiation rays being close to the edges of the collimator assembly.

In some embodiments, the penumbra characteristics regarding the edges of the collimator assembly may be determined based on a look-up table. In some embodiments, the look-up table may be determined by obtaining penumbra characteristics regarding the edges of the collimator assembly at one or more conditions and recording the obtained penumbra characteristics and the corresponding conditions in the look-up table. The one or more conditions may relate to at least one element of the collimator assembly (e.g., a leaf of the MLC, an X-jaw, a Y-jaw, etc.), an edge of the collimator assembly (e.g., a front edge, a side edge, etc.), an end edge position of at least one element of the collimator assembly (e.g., an end edge position of a leaf of the MLC, a position of an X-jaw), a position along an edge (e.g. Y-position along X-jaw), a thickness of a phantom or the subject, beam quality (e.g., an energy spectrum of the radiation beam, noise filtration, etc.), a detector response function, a field size (e.g., an average dimension of a treatment field of an irregular shape), or the like, or any combination thereof. As used herein, a front edge of an element (e.g., a leaf of the MLC, a jaw, etc.) of the collimator assembly may refer to an edge of the element that is closer to a central axis of the radiation beam. As used herein, a side edge of the element may refer to an edge of the element that connects to the front edge of the element. As used herein, an end edge may refer to an edge of the element that is opposite to the front edge of the element. The end edge position of at least one element of the collimator assembly (e.g., an end edge position of a leaf of the MLC, a position of an X-jaw) may refer to the position of the end edge of the at least one element of the collimator assembly.

Merely for illustration purposes, a collimator assembly including an MLC and at least one jaw may be taken as an example. Widths of the penumbra region corresponding to an end edge of a leaf under the conditions that a radiation beam traverses a different phantom of a plurality of phantoms each time may be determined based on images (e.g., EPID images) of each of the plurality of phantoms. In some embodiments, the phantoms may be water phantoms. Thicknesses of the plurality of phantoms may vary in a certain range, for example, from 5 centimeters to 50 centimeters. A correspondence relationship between widths of the penumbra region and corresponding thicknesses of the plurality of phantoms may be obtained. The correspondence relationship may be recorded in the look-up table. The look-up table may be stored in a storage device of the RT system 100 (e.g., the storage device 150, the storage device 220, etc.). In some embodiments, the correspondence relationship may be recorded in sub-tables of the look-up table. A sub-table may also be referred to as a penumbra table regarding the end edge of a specific leaf of a collimator assembly. Also, a penumbra table regarding a side edge of a specific leaf of the collimator assembly may be generated. Similarly, penumbra tables regarding end edges and side edges of other leaves of the MLC may be generated. In some embodiments, penumbra tables regarding the end edges and side edges of the leaves of the MLC under the conditions that the leaves are located at different positions may be generated. Similarly, penumbra tables regarding at least one jaw (e.g., at least one of X-jaws and Y-jaws) under the conditions that the at least one jaw is located at different positions may be generated. The position of a jaw may include a position of an end edge of the jaw and a position of the jaw (a position of the jaw assessed based on, e.g., a center or a center line of the jaw, a side edge of the jaw, etc.) relative to an edge of a leaf of the MLC.

For example, a water phantom having a thickness of 2 centimeters may correspond to a penumbra region regarding an end edge of a leaf of an MLC having a width of 4 millimeters, and another water phantom having a thickness of 20 centimeters may correspond to the penumbra region regarding the end edge of the same leaf of the MLC having a width of 7 millimeters. The correspondence relationship between the penumbra characteristics and thicknesses of the water phantoms may be recorded in the look-up table.

Generally, the one or more conditions may also relate to a size and a shape of the treatment field. The correspondence relationship between the penumbra characteristics and the size and/or shape of the treatment field may be approximated via, for example, a mean field diameter (e.g., the treatment field has a shape of a circle or a rough circle), a mean length, a mean width, or a combination thereof, of the treatment field.

In some embodiments, the penumbra characteristics regarding the edges of the collimator assembly under at least a part of the one or more conditions may be determined. In some embodiments, the way that the penumbra characteristics regarding the edges of the collimator assembly under the at least a part of the one or more conditions are determined may be similar to that of the examples regarding the plurality of phantoms with different thicknesses as exemplified above.

It should be noted that the look-up table is provided for illustration purposes, and not intended to be limiting. In some embodiments, the correspondence relationship between widths of the penumbra region and corresponding thicknesses of the plurality of phantoms may be recorded in a storage device of the RT system 100 (e.g., the storage device 150, the storage device 220, etc.) in the form of one or more curves. Such a curve may also be referred to as a penumbra curve regarding the end edge of a leaf of the MLC of the collimator assembly. Also, penumbra curves regarding end edges and side edges of other leaves of the MLC of the collimator assembly may be generated. In some embodiments, penumbra curves regarding the end edges and side edges of the leaves of the MLC under the conditions that the leaves are located at different positions may also be generated. Similarly, penumbra curves regarding at least one jaw (e.g., at least one of X-jaws and Y-jaws) under the conditions that the at least one jaw is located at different positions may also be generated.

In some embodiment, if the subject is a biological subject (e.g., a human, an animal), a thickness of an anatomical structure of a subject (e.g., a patient) that a radiation ray needs to traverse may be represented by a medium-equivalent thickness, such as a water-equivalent thickness (WET) value. Exemplary media may include water, bone, soft tissue, or the like, or any combination thereof. In some embodiments, the WET value may also serve as a condition or index of the look-up table. More details regarding the WET values of the subject along edges of a treatment field may be found elsewhere in the present disclosure. See, for example, FIGS. 7A and 7B and the descriptions thereof.

In some embodiments, after the penumbra characteristics regarding the edges of the collimator assembly under at least one of the one or more conditions are determined, the processing device 140 may establish the penumbra model based on the penumbra characteristics regarding the edges of the collimator assembly under the at least one of the one or more conditions. In some embodiments, the penumbra model may be constituted by, for example, results of the forward transport simulation and/or the simplified forward transport simulation, the look-up table, or the like, or any combination thereof. After the penumbra model is established, the inversely-attenuated primary images of the subject may be determined based at least in part on the penumbra model.

In some embodiments, simulations and/or previous measurements of the penumbra characteristics from one or more users regarding the edges of the collimator assembly under various conditions may also be recorded and serve as a part of the penumbra model. For example, a previous measurement from a first user under a condition that "thickness of soft tissue: 20 centimeters, thickness of bone: 5 centimeters, average field dimension: 5 centimeters, and beam energy: 6MV" may be recorded in the look-up table. If a second user analyzes a ray path of thickness of soft tissue: 22 centimeters and thickness of bone: 4 centimeters, and inputs the two values into the penumbra model, the processing device 140 may retrieve the previous measurement from the first user if the thickness of soft tissue and the thickness of bone in the previous measurement from the first user is closest to the input of the second user compared to other entries in the look-up table. Then corresponding penumbra characteristics in the previous measurement from the first user may be retrieved and provided to the second user.

In 550, the processing device 140 (e.g., the dose estimation module 430) may estimate a dose delivered to the subject based on the inversely-attenuated primary images of the subject.

In some embodiments, the processing device 140 may determine an input fluence map based on the inversely-attenuated primary images of the subject. The input fluence map may represent the amount of radiation passing through a spatial region. In some embodiments, the input fluence map determined based on the inversely-attenuated primary images of the subject may be presented in the form of a matrix that covers a spatial region (e.g., the input fluence plane). For each point in the input fluence plane, the input fluence map may define the amount of radiation passing through the point.

The processing device 140 may estimate the dose delivered to the subject by inputting the input fluence map into a forward dose calculation algorithm. In some embodiments, the forward dose calculation algorithm may account for factors associated with the radiation treatment, such as features of the radiation beam (e.g., beam quality, beam shape, etc.), a geometry and position of at least one element of the collimator assembly, the subject (e.g., inhomogeneities in the subject), scattering, dose leakage, etc. The actual dose delivered to the subject may be estimated according to the forward dose calculation algorithm.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. In some embodiments, the process 500 may be accomplished with one or more additional operations not described and/or without one or more of the operations discussed above. However, those variations and modifications do not depart from the scope of the present disclosure.

In some embodiments, the processing device 140 may determine attenuation of a beamlet in the radiation beam along the beam path based on a CT image of the subject (e.g., a planning image) and an input spectrum of energy. The beamlet as used herein may be any one of a plurality of beamlets (e.g., hundreds of beamlets), which are obtained by subdividing the radiation beam into a plurality of portions.

In some embodiments, a beamlet may include one or more radiation rays. In some embodiments, the attenuation of the beamlet may be energy dependent (e.g., as a function of energy). Since the radiation rays in the radiation beam are polychromatic as for attenuation during transit and detection efficiency by a detector, an effective attenuation factor may be obtained if the transit and detection of the polychromatic radiation rays are folded into a detector energy response function. By folding the transit and detection of the polychromatic radiation rays into the detector energy response function, the effects of the attenuation during transit and detection efficiency by a detector may be eliminated or reduced. The effective attenuation factor may be used to map an intensity of a measured image onto an input fluence value. In some embodiments, the input fluence value may be equal to $\hat{w}_k$, which denotes input radiation in a region k.

In some embodiments, penumbra characteristics of edges of a specific treatment field that traverses a specific subject may be calculated based on a beam model of the radiation beam, a shape of the treatment field, and an image (e.g., a planning image or a treatment image) of the specific subject. The penumbra characteristics may be associated with the edges of the collimator assembly that defines the treatment field for the subject. In some embodiments, the penumbra characteristics may need to be calculated once for each treatment field. In some embodiments, the penumbra characteristics may be precalculated any time after the treatment plan is made.

Figure 7A:
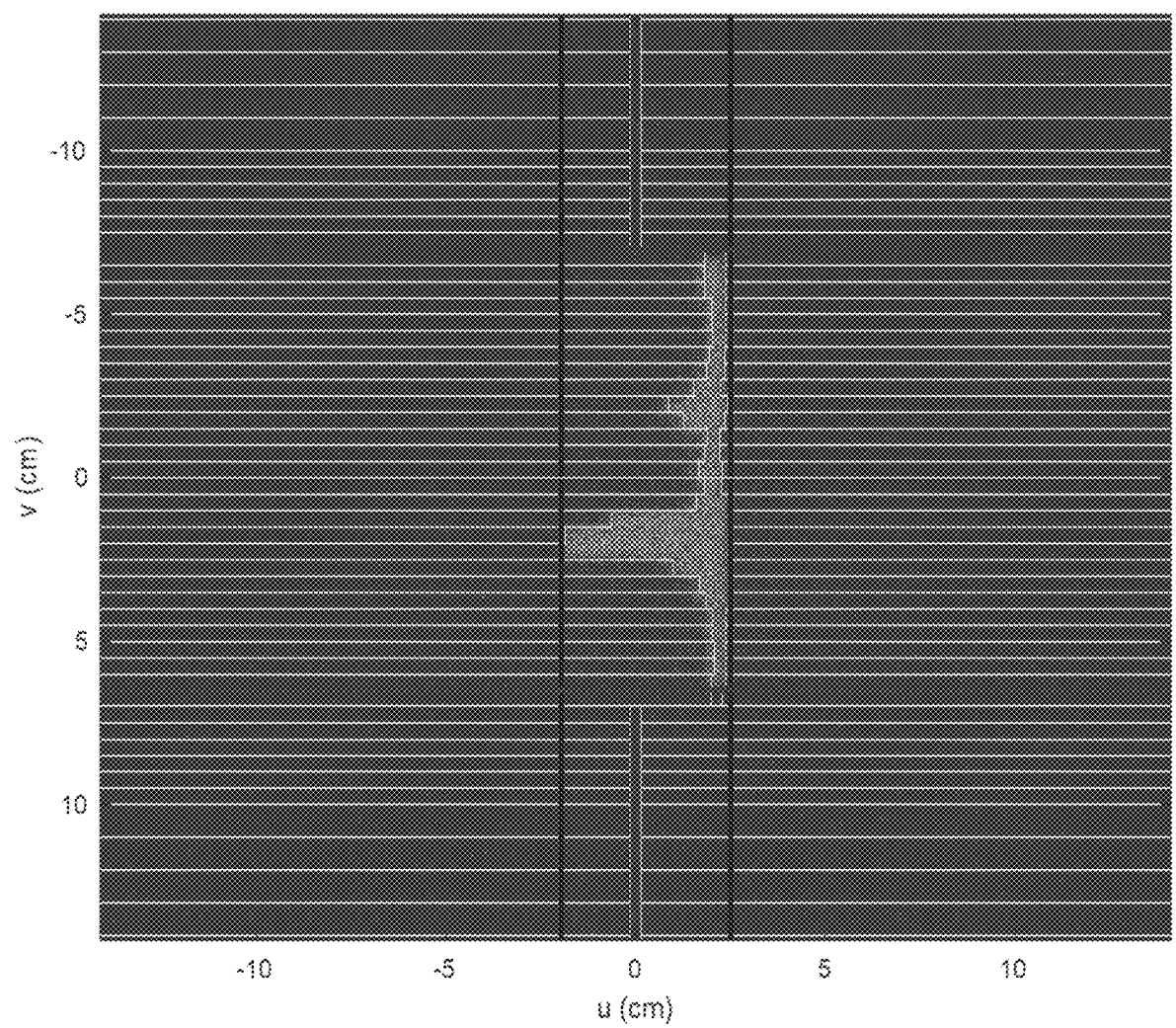
FIGS. 7A and 7B illustrate an exemplary treatment field collimated by two pairs of jaws and an MLC according to some embodiments of the present disclosure.
Figure 7B:
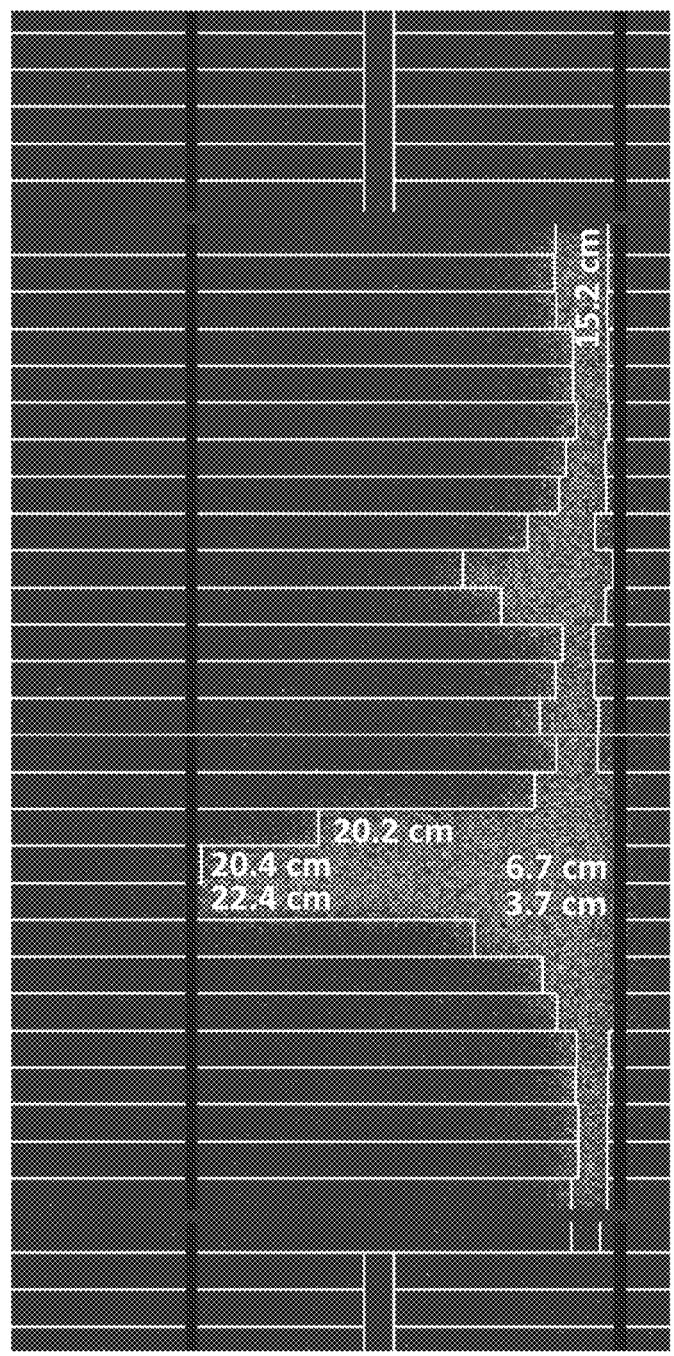

FIGS. 7A and 7B illustrate an exemplary treatment field collimated by two pairs of jaws and an MLC according to some embodiments of the present disclosure. The treatment field shown in FIGS. 7A and 7B may be projected onto an isocentric plane, which passes through a system isocenter (e.g., an isocenter of the RT device 110, which may be located on a rotation axis of the gantry 111 of the imaging component 113). The WET values of the subject close to edges of one or more elements of the collimator assembly within the treatment field may be determined. Merely for illustration purposes, as illustrated in FIG. 7B, within which the WET values are indicated close to corresponding elements of the collimator assembly, a WET value of the subject being close to a field edge that corresponds to an upper Y-jaw is 15.2 centimeters, WET values of the subject close to field edges that correspond to three left leaves of the MLC are 20.2 centimeters, 20.4 centimeters, and 22.4 centimeters, respectively. WET values of the subject close to field edges that correspond to two right leaves of the MLC are 6.7 centimeters and 3.7 centimeters, respectively. The WET values may be determined based on paths of radiation rays that travel close to edges of corresponding elements of the collimator assembly.

It should be noted that the WET values of the subject are provided merely for illustration purposes, and not intended to be limiting. In some embodiments, a pathlength of a radiation ray within the subject may be divided into one or more segments based on a CT image of the subject. Each segment may include a pathlength through a certain tissue type (e.g., soft tissue, lung tissue, bone, air, etc.). For example, a radiation ray with a pathlength of 25 centimeters within the subject may be divided into two segments. The two segments may include a first segment of WET of 15.2 centimeters and a second segment of bone-equivalent thickness of 8.1 centimeters. In some embodiments, different tissue types may be identified based on HU values (e.g., a calibration curve of HU values to the electron density for a CT image of the subject). In some embodiments, the dimensions or lengths of the one or more segments corresponding to tissue of different types may also be used as parameters in the look-up table. For example, the look-up table may include dimensions or indexes of a water-equivalent thickness and a cortical-bone-equivalent thickness. In some embodiments, a width of the penumbra region corresponding to bone having a certain thickness may be larger than that corresponding to soft tissue having a same thickness.

Figure 8:
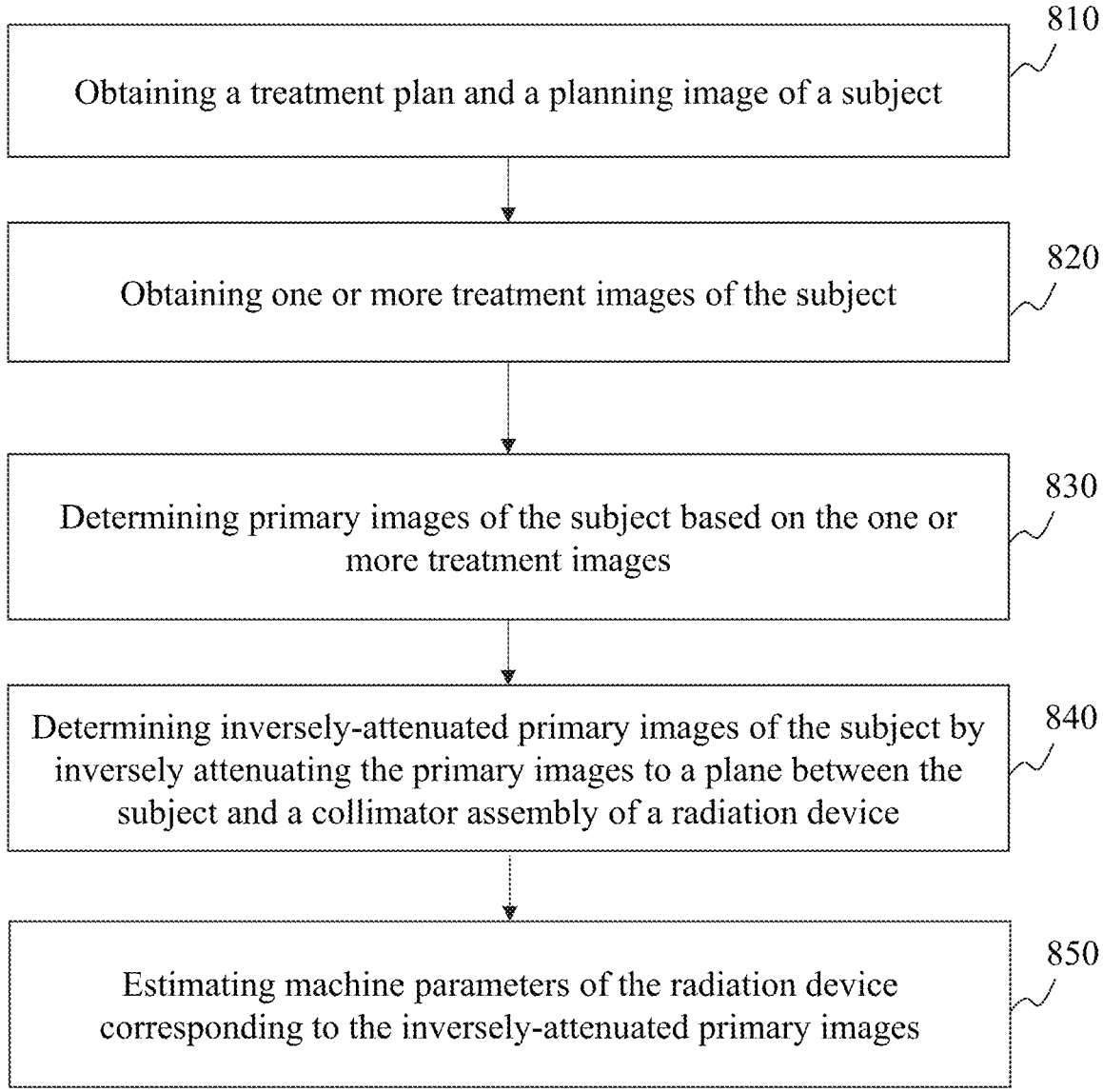
FIG. 8 includes a flowchart illustrating an exemplary process for estimating machine parameters of a radiation device according to some embodiments of the present disclosure.

FIG. 8 includes a flowchart illustrating an exemplary process for estimating machine parameters of a radiation device according to some embodiments of the present disclosure. In some embodiments, process 800 may be executed by the RT system 100. For example, the process 800 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 800.

In 810, the processing device 140 (e.g., the obtaining module 410) may obtain a treatment plan and a planning image of a subject. In some embodiments, the operation 810 may be similar to or the same as the operation 510 of the process 500 as illustrated in FIG. 5, the description of which is not repeated here.

The planning image may be generated in a planning stage of a radiation treatment. For example, before the radiotherapy treatment (e.g., days or weeks before the treatment commences) is performed on the subject, the planning image of the subject may be acquired using an imaging device (e.g., the imaging component 113 of the RT device 110, or an imaging device other than the imaging component 113).

In some embodiments, the planning image may be a CT image generated by scanning the subject using a CT scanner. In some embodiments, the CT scanner may be a CBCT scanner and/or an MSCT scanner. The CBCT scanner may perform a CBCT scan of a subject. The MSCT scanner may perform an MSCT scan of a subject. The images generated based on the CBCT scan or the MSCT scan may be stored in a storage device (e.g., the storage device 150, the storage device 220, or an external storage device) associated with the RT system 100 for radiation therapy planning.

The treatment plan may be made before a radiation treatment is applied to the subject. In some embodiments, the treatment plan may be made based on the planning image. For example, tissue attenuation values of the subject may be estimated based on the planning image. The estimated tissue attenuation values may be converted to electron densities and used to estimate the planned radiation dose to be applied on the radiation target.

In 820, the processing device 140 (e.g., the obtaining module 410) may obtain one or more treatment images of the subject. In some embodiments, the operation 820 may be similar to or the same as the operation 520 of the process 500 as illustrated in FIG. 5, the description of which is not repeated here.

In some embodiments, scanning data from one or more scans of the subject may be acquired. In some embodiments, the one or more scans may be performed on the subject during one or more of the treatment fractions. The one or more treatment images may be generated based on the acquired scanning data.

In some embodiments, the one or more treatment images may be EPID images. The EPID images may be generated by an EPID. The EPID may be positioned in the pathway of a radiation beam in a radiation treatment.

In 830, the processing device 140 (e.g., the processing module 420) may determine primary images of the subject based on the one or more treatment images. In some embodiments, the operation 830 may be similar to or the same as the operation 530 of the process 500 as illustrated in FIG. 5, the description of which is not repeated here.

The primary images may be obtained by removing at least a portion of the scatter component from the one or more treatment images. In some embodiments, the primary images may be determined by performing a scatter correction on the treatment images. Exemplary scatter correction techniques may include a convolution technique, a deconvolution technique, an ordered subsets convex technique, a beam-stop measurement technique, or the like, or any combination thereof.

In some embodiments, the primary images may be determined by subtracting the scatter component from the one or more treatment images. In some embodiments, the scatter component may be estimated according to a scatter simulation technique or algorithm, such as a Monte Carlo (MC) simulation, a kernel-based algorithm, a scatter-to-primary ratio (SPR), etc.

In 840, the processing device 140 (e.g., the processing module 420) may determine inversely-attenuated primary images of the subject by inversely attenuating the primary images to a plane between the subject and a collimator assembly of a radiation device. In some embodiments, the operation 840 may be similar to or the same as the operation 540 of the process 500 as illustrated in FIG. 5, the description of which is not repeated here.

Penumbra characteristics regarding edges of one or more elements of the collimator assembly may be determined. In some embodiments, the penumbra characteristics regarding the edges of the collimator assembly may be determined based on a forward transport of the treatment field through the subject (also referred to as forward transport simulation for brevity). In some embodiments, the forward transport simulation may be implemented by an MC simulation, a Boltzmann transport algorithm, or the like, or a combination thereof. In some embodiments, the penumbra characteristics regarding the edges of the collimator assembly may be determined based on a simplified forward transport simulation. In some embodiments, the simplified forward transport simulation may be similar to or the same as the forward transport simulation exemplified above except that scatter estimation in the simplified forward transport simulation may be simplified. In some embodiments, the scatter estimation in the simplified forward transport simulation may be implemented by a kernel based algorithm. In some embodiments, the penumbra characteristics regarding the edges of the collimator assembly may be determined based on a look-up table. In some embodiments, the look-up table may be determined by obtaining penumbra characteristics regarding the edges of the collimator assembly under one or more conditions and recording the obtained penumbra characteristics and the corresponding conditions in the look-up table.

After the penumbra characteristics regarding the edges of the collimator assembly under at least one of the one or more conditions are determined, the processing device 140 may establish the penumbra model based on the penumbra characteristics regarding the edges of the collimator assembly under the at least one of the one or more conditions. In some embodiments, the penumbra model may be constituted by, for example, results of the forward transport simulation and/or the simplified forward transport simulation, the look-up table, or the like, or any combination thereof. After the penumbra model is established, the inversely-attenuated primary images of the subject may be determined based at least in part on the penumbra model.

In 850, the processing device 140 (e.g., the machine parameter determination module 440) may estimate machine parameters of the radiation device corresponding to the inversely-attenuated primary images.

The machine parameters of the radiation device (e.g., the RT device) may include, for example, positions of a gantry of the radiation device (e.g., the gantry 118 of the treatment component 116), a shape of the collimator assembly of the radiation device (e.g., the RT device 110), a geometry and/or position of at least one element of the collimator assembly, or the like, or any combination thereof. In some embodiments, the machine parameters of the radiation device may be determined according to an optimazation function, for example, Equation (1):

$$\hat{C}_\Gamma^n = \underset{C}{\operatorname{argmin}} \int du \Big[ \kappa \int dE\ d(E)\Phi_{\Gamma^n}(u, E; C)_{ent} - \hat{M}_{primary\_entrance}^{pa} \Big]^2, \quad (1)$$

where C may denote the machine parameters, $\Gamma_n$ may denote a beam shape of an n-th fraction of a treatment plan, u may denote a plane, which has in-plane coordinates (u,v) and a normal coordinate w along a central axis the radiation beam, $\kappa$ may denote a scaling factor between a measured image and a synthetic image, E may denote the energy of the particles or photons in the radiation beam, d(E) may denote a detector model, $\Phi_{\Gamma^n}(u,E; C)_{ent}$ may denote a beam model at an entrance fluence space, and $\hat{M}_{primary\_entrance}^{pa}$ denotes the estimated primary image after inverse attenuation through the subject (e.g., a patient, a phantom, etc.), that is estimated from a treatment image (e.g., an EPID image). In some embodiments, the machine parameters C may be a vector including various combinations of the parameters of the RT device 110 as exemplified above. The scaling factor $\kappa$ between a measured image and a synthetic image may be equal to a ratio of a value of a pixel in the measured image based on a signal detected by a real detector (or an average value of multiple pixels in the measured image) and a value of a corresponding pixel in a synthetic image which may be estimated based on a simulated detector (or an average value of multiple pixels in the synthetic image). The synthetic image may describe radiation energy deposited in the plane of the simulated detector. The detector model d(E) may be used to approximate a detector response to incident particles or photons, neglecting (in this simplified example) the effects of different angles of incidence of the particles with respect to the detector (e.g., a detector plane) and the positions where the particles or photons impinge on the detector plane. In general, the effects of particle incidence angle and optical scatter [glare] in the detector may be included in this model. The entrance fluence space may be a plane situated at a location at or before the beam enters the subject, which is perpendicular to the beam central axis. In some embodiments, the beam model $\Phi_{\gamma^n}(u, E; C)_{ent}$ may be determined based on the penumbra model. In some embodiments, $\hat{M}_{primary\_entrance}^{pa}$ may be the value of a square pixel.

In some discrete embodiments, $\hat{M}_{primary\_entrance}^{pa}[k]$ may represent the value of the k-th region in a processed measured image, and $\Phi_{\gamma^n}^k(E; C)_{ent}$ may represent the input fluence contributing or corresponding to region k. The machine parameters of the radiation device may be determined according to Equation (2):

$$\hat{C}_\Gamma^n = \underset{\operatorname{argmin}}{C} \sum \Big[ \kappa \int dE\ d(E)\Phi_{\Gamma^n}^k(E; C)_{ent} - \hat{M}_{primary\_entrance}^{pa}[k] \Big]^2. \quad (2)$$

More details regarding the parameters in Equations (1) and (2) can be found in, e.g., U.S. patent application Ser. No. 16/615,004, filed on Oct. 18, 2019, the contents of which are hereby incorporated by reference.

Solutions of Equation (1) may be used to estimate the machine parameters by iteratively synthesizing images for vectors of different values of machine parameters C with the objective of minimizing a discrepancy between input radiation estimated from a synthetic image and a treatment image. In some embodiments, a plurality of iterations may be performed for reducing the discrepancy. In some embodiments, during each of the plurality of iterations, a gantry position of the gantry 118 may be scheduled. The gantry position may be associated with a sequence of MLC shapes, jaw positions, collimator angles, etc. After the plurality of iterations are performed, an optimized gantry position corresponding to a smallest discrepancy determined in the plurality of iterations may be determined. Then other machine parameters associated with the optimized gantry position may be determined. The estimated machine parameters may correspond to a planned radiation dose to be delivered to the subject, which may be provided in the treatment plan.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. In some embodiments, the process 500 may be accomplished with one or more additional operations not described and/or without one or more of the operations discussed above. However, those variations and modifications do not depart from the scope of the present disclosure. For example, in an ideal case that the widths of the penumbra region is not affected by the subject (e.g., a patient or a phantom), the beam shape model $\Phi_{\gamma^n}(u, E; C)_{ent}$ may be derived from $\hat{M}_{primary\_entrance}^{pa}[k]$, and an intensity distribution of the radiation beam may exhibit a beam shape before the radiation beam enters the subject.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system, comprising:
   at least one storage device including a set of instructions; and
   at least one processor configured to communicate with the at least one storage device, wherein when executing the set of instructions, the at least one processor is configured to direct the system to perform operations including:
      obtaining a treatment plan and a planning image of a subject;
      obtaining one or more treatment images of the subject, wherein the one or more treatment images are generated by performing at least a portion of the treatment plan including delivering at least a radiation beam towards the subject using a radiation device;
      determining primary images of the subject based on the one or more treatment images;
      determining inversely-attenuated primary images of the subject by inversely attenuating the primary images to a plane located between the subject and a collimator assembly of the radiation device; and
      estimating machine parameters of the radiation device corresponding to the inversely-attenuated primary images.

2. The system of claim 1, wherein the one or more treatment images includes electronic portal imaging device (EPID) images.

3. The system of claim 1, wherein the determining inversely-attenuated primary images of the subject by inversely attenuating the primary images to a plane between the subject and a collimator assembly of the radiation device includes:
   obtaining a penumbra model associated with penumbra characteristics of edges of the collimator assembly; and
   determining the inversely-attenuated primary images of the subject by inversely attenuating the primary images to the plane based at least in part on the penumbra model.

4. The system of claim 3, wherein the penumbra characteristics of the edges of the collimator assembly are determined based on a look-up table, wherein the look-up table relates to at least one of a medium-equivalent thickness of the subject, one or more elements of the collimator assembly, a position of each of at least one element of the collimator assembly, or beam quality of the radiation device.

5. The system of claim 4, wherein the look-up table further relates to a plurality of tissue types and a dimension of each of at least one of the plurality of tissue types of the subject.

6. The system of claim 3, wherein the penumbra characteristics of edges of the collimator assembly are determined based on a forward transport of a treatment field through the subject.

7. The system of claim 6, wherein the forward transport includes a Monte Carlo simulation or a Boltzmann transport algorithm.

8. The system of claim 6, wherein the forward transport has a perturbation range associated with penumbra regions in the one or more treatment images.

9. The system of claim 6, wherein scatter in the forward transport is determined according to a kernel based algorithm.

10. The system of claim 1, the operations further including:
    determining an input fluence map based on the inversely-attenuated primary images of the subject; and
    determining an estimate of a dose delivered to the subject by inputting the input fluence map into a forward dose calculation algorithm.

11. The system of claim 1, wherein the machine parameters correspond to a planned dose to be delivered to the subject.

12. A system, comprising:
    at least one storage device including a set of instructions; and
    at least one processor configured to communicate with the at least one storage device, wherein when executing the set of instructions, the at least one processor is configured to direct the system to perform operations including:
        obtaining a treatment plan and a planning image of a subject;
        obtaining one or more treatment images of the subject, wherein the one or more treatment images are generated by performing at least a portion of the treatment plan including delivering at least a radiation beam towards the subject using a radiation device;
        determining primary images of the subject based on the one or more treatment images;
        determining inversely-attenuated primary images of the subject by inversely attenuating the primary images to a plane located between the subject and a collimator assembly of the radiation device based at least in part on a penumbra model associated with penumbra characteristics of edges of the collimator assembly; and
        determining an input fluence map based on the inversely-attenuated primary images of the subject; and
        estimating a dose delivered to the subject by inputting the input fluence map into a forward dose calculation algorithm.

13. A method implemented on a computing device having a processor and a computer-readable storage device, the method comprising:
    obtaining a treatment plan and a planning image of a subject;
    obtaining one or more treatment images of the subject, wherein the one or more treatment images are generated by performing at least a portion of the treatment plan including delivering at least a radiation beam towards the subject using a radiation device;
    determining primary images of the subject based on the one or more treatment images;
    determining inversely-attenuated primary images of the subject by inversely attenuating the primary images to a plane located between the subject and a collimator assembly of the radiation device; and
    estimating machine parameters of the radiation device corresponding to the inversely-attenuated primary images.

14. The method of claim 13, wherein the one or more treatment images includes electronic portal imaging device (EPID) images.

15. The method of claim 13, wherein the determining inversely-attenuated primary images of the subject by inversely attenuating the primary images to a plane between the subject and a collimator assembly of the radiation device includes:
    obtaining a penumbra model associated with penumbra characteristics of edges of the collimator assembly; and
    determining the inversely-attenuated primary images of the subject by inversely attenuating the primary images to the plane based at least in part on the penumbra model.

16. The method of claim 15, wherein the penumbra characteristics of the edges of the collimator assembly are determined based on a look-up table, wherein the look-up table relates to at least one of a medium-equivalent thickness of the subject, one or more elements of the collimator assembly, a position of each of at least one element of the collimator assembly, or beam quality of the radiation device.

17. The method of claim 16, wherein the look-up table further relates to a plurality of tissue types and a dimension of each of at least one of the plurality of tissue types of the subject.

18. The method of claim 15, wherein the penumbra characteristics of edges of the collimator assembly are determined based on a forward transport of a treatment field through the subject.

19. The method of claim 18, wherein the forward transport has a perturbation range associated with penumbra regions in the one or more treatment images.

20. The method of claim 13, further including:
    determining an input fluence map based on the inversely-attenuated primary images of the subject; and
    determining an estimate of a dose delivered to the subject by inputting the input fluence map into a forward dose calculation algorithm.

* * * * *